United States Patent

Sellstedt et al.

[11] 3,937,719
[45] Feb. 10, 1976

[54] (4-OXO-4H-1-BENZOPYRAN-2-YL)-OXAMIC ACID, SALTS AND ESTERS ANTI-ALLERGIC AGENTS

[75] Inventors: John H. Sellstedt, Pottstown; Dieter H. Klaubert, West Chester, both of Pa.

[73] Assignee: American Home Products Corporation, New York, N.Y.

[22] Filed: Jan. 6, 1975

[21] Appl. No.: 538,672

[52] U.S. Cl. ............ 260/345.2; 260/345.5; 424/283
[51] Int. Cl.² ........................................ C07D 311/02
[58] Field of Search ...................... 260/345.2, 345.5

[56] References Cited
UNITED STATES PATENTS

| | | | |
|---|---|---|---|
| 3,322,795 | 5/1961 | Ellis et al. | 260/345.2 |
| 3,652,765 | 3/1972 | Ellis et al. | 260/345.2 |
| 3,836,541 | 9/1974 | Johnson et al. | 260/326.2 |
| 3,862,143 | 1/1975 | Klectchko et al. | 260/345.2 |

*Primary Examiner*—Bernard Helfin
*Assistant Examiner*—G. Breitenstein
*Attorney, Agent, or Firm*—Richard K. Jackson

[57] ABSTRACT

Anti-allergic agents present the following structural formula:

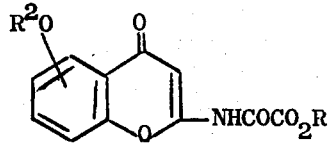

in which
R is —H, lower alkyl or an alkali metal cation.
$R^2$ is alkyl of 1 to 6 carbon atoms or hydroxyalkyl of 2 to 6 carbon atoms.

5 Claims, No Drawings

(4-OXO-4H-1-BENZOPYRAN-2-YL)-OXAMIC ACID, SALTS AND ESTERS ANTI-ALLERGIC AGENTS

BACKGROUND OF THE INVENTION

Atopic immediate sensitivity is the chief manifestation found in animals suffering from bronchial asthma, seasonal pollinosis, allergic rhinitis, urticaria, allergic conjunctivitis, food allergy and anaphylactoid reactions. The substances most frequently responsible for clinically manifest sensitivities are plant pollen, animal feathers and danders, dust, milk and wheat, whether inhaled or ingested.

Atopic hypersensitivity is found in man, dog and other animals. Its occurrence is exceptionally found in the lower animals.

The presence of antibodies associated with atopic reactions in the host serum is established by the passive sensitization of the skin of a normal recipient, after injection of serum from a sensitized host into a skin site followed by injection of antigen into the same area 24 hours later, resulting in a local hive. This is commonly referred to as the Prausnitz-Kustner (P-K) reaction.

The antibody associated with atopic hypersensitivity possesses distinctive features in that it does not in all forms precipitate with its antigen, fails to pass the placenta from mother to fetus, has special affinity for the skin, frequently lacks specificity toward an individual antigen in an individual sensitized by a variety of antigenic factors and is usually labile at about 56°C after 2 hours.

The homocytotropic antibody found in or induced in the rat is related in function and reaction to immunoglobulin E (reagin or IgE) found in the human. The correlation between homocytotropic antibody in the rat and IgE in the human has been established through the common effects obtained from chemical reactions, immunological reactions and drug responses in the two species hosting those antibodies. In the human, reagin is the antibody responsible for atopic immediate hypersensitive reactions. In the rat, the homocytotropic antibody is responsible for atopic immediate hypersensitive reactions.

In theory, reagin, influences the cell membrane of a mast cell by reacting with an antigen, to initiate the reaction(s) within the mast cell which ultimately releases a mediator such as Bradykinin, SRS-A (slow reacting substance-A), histamine, and other unknown substances. The mediator effects a change in surrounding cell wall permeability permitting a rapid change in flow or exudance of mediator(s) from the cells, resulting in an allergic attack symptom. The various methods commonly employed to relieve the symptoms of allergic attack, none of which are considered to be quite acceptable, are to (1) avoid attack by the antigen, (2) block the production of antibody with an immunosuppressant, (3) block the action of the mediators on the cell under attack by administration of anti-histaminics, anti-5-hydroxy-tryptamine (5-HT) or anti-inflammatories, or (4) stimulate the cell under attack to negate the action of the mediator through the action of bronchodilators such as Isoprel or a Xanthine.

The only commercial compound known to date to operate as an anti-allergic primarily by blocking reaction(s) within the mast cells, thereby preventing the production and release of mediators, is disodium cromoglycate (INTAL).

DESCRIPTION OF THE INVENTION

In accordance with this invention there is provided a method for suppressing the manifestations of atopic immediate sensitivity in a sensitized animal which comprises administering to said animal an effective amount of a compound of the formula:

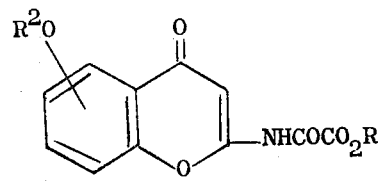

in which
R is —H, alkyl of 1 to 6 carbon atoms, or an alkali metal cation and
$R^2$ is alkyl of 1 to 6 carbon atoms or hydroxyalkyl of 2 to 6 carbon atoms.

In addition, this invention provides novel chemical compounds of the above described formula.

The compounds of this invention have been demonstrated to relieve allergic manifestations when administered intraperitoneally and orally to sensitized rats. The technique employed to establish the anti-allergic activity of the disclosed compounds is reported in Immunology, vol. 16, pp. 749–760 (1969) and involves four male Charles River rats (200–250 grams body weight) per group to provide a control, a host for administration of a standard anti-allergic compound (disodium cromoglycate) and animals for the test compound. The rats are injected intracutaneously on their shaved backs with sera from rats immunized with egg albumin and pertussis vaccine. Twenty-four hours after the initial injections, the test compound is administered intraperitoneally or orally at a maximum dosage level of 200 milligrams per kilogram host body weight. Five minutes later one milliliter of a 0.5 percent solution of Evans blue dye and 8 milligrams of egg albumin is injected intravenously. After 40 minutes, the animal is sacrificed and the bleb size on its back is measured. The mean bleb size for the animals administered the test compound is calculated and the percent inhibition is determined by comparison with the control animal.

Although the mechanism by which the compounds of this invention function is not absolutely known, applicants have found that the compounds of this invention, in a manner believed to be similar to the function of INTAL, block reaction(s) in the mast cell leading to the production and release of mediators.

The compounds of this invention permit the occurrence of a non-productive antigen-antibody interaction by effectively blocking the IgE type reaction.

In sum, the compounds of this invention block the release of mediators commonly resulting from the antigen antibody reaction as exemplified in a passive cutaneous anaphylaxis test (PCA) using rat homocytotropic antibody — a known correlate of human reaginic antibody.

By analogy to disodium cromoglycate and its activity correlation between standard test animals, domestic animals and man, the compounds of this invention have been established as anti-allergic agents suitable for the same uses at analogous doses and through the same routes of administration as INTAL.

Thus, there is provided herewith a method for suppressing allergic manifestations of atopic immediate sensitivity in warm-blooded human and non-human animals, the latter including domesticated animals such as the mouse, rat, hamster, gerbil, dog, cat, sheep, goat, horse, cow, and the like by administering an effective amount of one or more of the compounds disclosed in this application by oral, topical, intraperitoneal, intramuscular or intravenous routes. The compounds of this invention may be administered in conjunction with known compounds effecting anti-histaminic, anti-hypertensive, analgesic, central nervous system depressant, immunosuppressive, anti-serotonin, anti-Bradykinin or endocrinological responses. In addition, those conventional adjuvants known to the art may be combined with the anti-allergics of this invention to provide compositions and solutions for administrative purposes, although it is considered desirable and feasible to employ the anti-allergics as neat or pure compounds without additives other than for purposes of providing suitable pharmaceutical solution or liquid or vapor suspensions.

The effective dose range in test animals has been established to be from about 20 milligrams per kilogram to a dosage resulting in substantially 100 percent prevention of the allergic response at 200 milligrams per kilogram host body weight upon administration, orally.

As an inhalant, the dose is analogous to that of INTAL, or about two milligrams administered as needed prior to attack. Thus, the dosage contemplated for human oral or intraperitoneal use based upon the potency of the compound administered lies from about 750 milligrams to 2 grams, preferable 1 gram to about 1½ grams in unit dosage form to be administered when necessary and to the degree of the desired response, in single or plural doses under the guidance of a physician.

EXAMPLE 1

(4-Oxo-4H-1-benzopyran-2-yl)Oxamic Acid Ethyl Ester

To a suspension of 1.61 grams (0.01 mole) of 2-amino-4H-1-benzopyran-4-one (prepared by the method of Kawase et al., Bull. Chem. Soc. Japan, 35, 1869(1962)) in 30 milliliters of methylene chloride, is added 0.8 grams (0.01 mole) of pyridine followed by the dropwise addition of 1.37 grams (0.01 mole) of ethyl oxalyl chloride in 20 milliliters of methylene chloride. The resulting solution is stirred for one hour, poured into distilled water and the organic layer separated, dried and evaporated to yield the title compound. Recrystallization from ethyl acetate gives 2.2 grams (80 percent yield) of the title compound, m.p. 167°–169°C.

Elemental Analysis for $C_{13}H_{11}NO_5$:
Calc'd: C, 59.76; H, 4.25; N, 5.36.
Found: C, 59.40; H, 4.09; N, 5.44.

The results obtained in the PCA rat test described above, demonstrate that at 200 milligrams per kilogram host body weight, intraperitoneal, the title compound exhibited 68 percent suppression of the allergic response. Orally, the title compound exhibited 62 per cent suppression of the allergic response at 20 milligrams per kilogram host body weight.

EXAMPLE 2

(4-Oxo-4H-1-benzopyran-2-yl)Oxamic Acid Sodium Salt

To a solution of 0.8 grams (0.02 mole) of sodium hydroxide in 20 milliliters of water is added 5.22 grams (0.02 mole) of the ethyl ester prepared in Example 1. The resulting solution is stirred for one half hour and the product is recovered by filtration, dried and recrystallized from ethanol-water to give 3 grams of the sodium salt monohydrate, m.p. 280°C. (decomp.). The water of hydration is removed on gently heating the product. Acidification of the sodium salt yields the free carboxylic acid.

Elemental Analysis for $C_{11}H_6NO_5Na.H_2O$:
Calc'd: C, 48.36; H, 2.95; N, 5.13.
Found: C, 48.13; H, 2.67; N, 5.18.

The sodium salt exhibited 55 percent suppression at 200 milligrams per kilogram host body weight, intraperitoneally, and 15 percent suppression at 20 milligrams per kilogram host body weight, orally, in the rat PCA test described, supra.

EXAMPLE 3

(6-Methoxy-4-Oxo-4H-1-Benzopyran-2-ylamino)Oxamic Acid, Ethyl Ester

A solution of 5-methoxysalicylic acid (33.6 g., 0.2 mol) in 300 ml. of hexamethylphosphorustriamide is treated successively with 16 g. of sodium hydroxide in 40 ml. of water and 68.4 g. (0.4 mol) of benzyl bromide. The resulting solution is stirred 14 hours at room temperature, poured into water and extracted with diethyl ether. The ether solution is dried and evaporated to a yellow oil which solidified on standing. Recrystallization from benzenehexane gives the desired 2-benzyloxy-5-methoxy benzoic acid benzyl ester.

To a solution of 10.1 g. (0.1 mol) of diisopropylamine in 200 ml. of tetrahydrofuran at −40°C. is added 66 ml. of 1.5 M. butyllithium in hexane (0.1 mol). After ½ hour, the solution is cooled to −76°C. and 4.1 g. (0.1 mol) of acetonitrile in 50 ml. of tetrahydrofuran is added dropwise. Stirring is continued for 1 hour, 17.4 g. (0.05 mol) of the benzyl ester prepared in the preceding paragraph is added and the solution is warmed to room temperature with stirring for an additional hour. The solution is poured into water, the organic layer is separated, washed with saturated aqueous NaCl, dried and evaporated to a solid which is recrystallized from diethyl ether yield, 7.5 g.; m.p. 98°–100°C.

Elemental Analysis for $C_{17}H_{15}NO_3$:
Calc'd: C, 72.58; H, 5.38; N, 4.98.
Found: C, 72.54; H, 5.42; N, 5.12.

A mixture of 2.81 g. (0.01 mol) of 2-benzyloxy-5-methoxy-phenylacetonitrile prepared in the preceding paragraph and 0.1 g. 5% Pd-BaSO₄ in 50 ml. of ethyl acetate is hydrogenated at atmospheric pressure until 1 equivalent of hydrogen is absorbed. Filtration through Celite, evaporation and recrystallization from diethyl ether gives 1.7 g. of 2-hydroxy-5-methoxy-phenylacetonitrile, m.p. 160°–165°C.

Elemental Analysis for $C_{10}H_9NO_3$:
Calc'd: C, 62.82; H, 4.75; N, 7.33.
Found: C, 62.49; H, 4.94; N, 7.41.

A solution of 1.11 g. (0.01 mol) of the product of the preceding paragraph in 50 ml. of diglyme is heated at reflux for 6 hours, cooled to 0°C. and the product is removed by filtration to give 1.6 g. of 2-amino-6-methoxy-4-oxo-4H-1-benzopyran, m.p. 275°–280°C. (decomp.)

Elemental Analysis for $C_{10}H_9NO_3$:
Calc'd: C, 62.82; H, 4.75; N, 7.33.
Found: C, 62.94; H, 4.85; N, 6.94.

This title compound is prepared by oxalation of the amine prepared in the preceding paragraph, following the procedure of Example 1, m.p. 213°–215°C.

Elemental Analysis for $C_{14}H_{13}NO_6$:
Calc'd: C, 57.73, H, 4.50; N, 4.82.
Found: C, 57.62; H, 4.58; N, 4.76.

EXAMPLE 4

[5-(2-Hydroxyethoxy)-4-Oxo-4H-1-benzopyran-2-yl]Oxamic Acid, Ethyl Ester 2-(2-Hydroxyethoxy)-6-nitrobenzonitrile is prepared by the dropwise addition of a tetrahydrofuran solution of lithium hydroxyethoxide to a tetrahydrofuran (500 ml.) solution of 2,6-dinitrobenzonitrile (19.3 g.) at reflux. After all the ethoxide is added, the reaction is refluxed for 4 hours, cooled and evaporated to dryness. The solid product is extracted with hot benzene, m.p. 140°–142°C.

The benzonitrile prepared in the preceding paragraph is reacted with sodium benzyloxide in tetrahydrofuran under standard conditions to displace the 6-nitro group with the benzyloxy substituent, followed by methanolysis of the nitrile with methanolic HCl to afford the methyl ester.

The carboxymethyl group is then displaced by the acetonitrile union formed with butyllithium and acetonitrile. The resulting 2-benzyloxy-6-hydroxyethoxy-phenylacetonitrile is hydrogenated over Pd/C to the corresponding phenol which is cyclized following the procedure of Example 3 to yield 2-amino-6-hydroxethoxy-4-oxo-4H-1-benzopyran.

The benzopyran in methylene chloride, is treated with four equivalents of pyridine followed by two equivalents of trimethylchlorosilane. After two hours, one equivalent of ethyl oxalylchloride is added. After twenty hours an excess of dilute HCl is added and the title compound is recovered with the organic layer which is dried and evaporated to yield the product.

What is Claimed is:

1. A compound of the formula

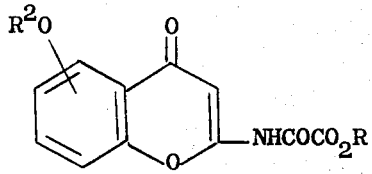

in which
R is —H, alkyl of 1 to 6 carbon atoms or an alkali metal cation and
$R^2$ is alkyl of 1 to 6 carbon atoms or hydroxyalkyl of 2 to 6 carbon atoms.

2. The compound of claim 1 which is

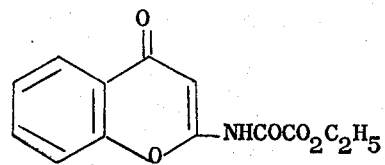

3. The compound of claim 1 which is

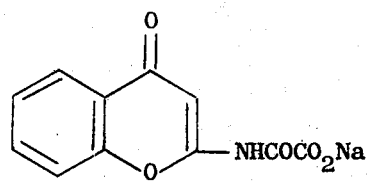

4. The compound of claim 1 which is

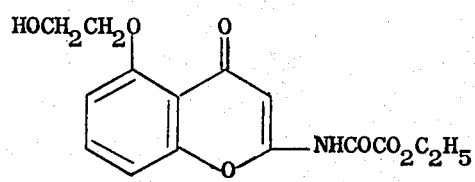

5. The compound of claim 1 which is

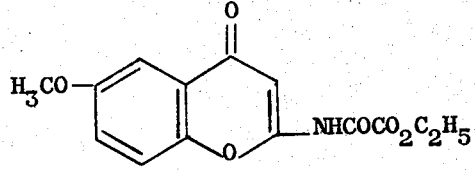

* * * * *